US012797509B2

(12) United States Patent
Loria

(10) Patent No.: US 12,797,509 B2
(45) Date of Patent: Nov. 17, 2026

(54) MULTIPLE VISCOSITY OIL-IN-WATER COMPOSITION USEFUL AS AN INJECTABLE FILLER AND A SCAFFOLD FOR COLLAGEN GROWTH

(71) Applicant: LORIA PHARMACEUTICAL, LLC, Doral, FL (US)

(72) Inventor: Victor Loria, Miami, FL (US)

(73) Assignee: LORIA PHARMACEUTICAL, LLC, Doral, FL (US)

( * ) Notice: Subject to any disclaimer, the term of this patent is extended or adjusted under 35 U.S.C. 154(b) by 397 days.

(21) Appl. No.: 18/037,223

(22) PCT Filed: Jan. 12, 2022

(86) PCT No.: PCT/US2022/012200

§ 371 (c)(1),
(2) Date: May 16, 2023

(87) PCT Pub. No.: WO2022/155261

PCT Pub. Date: Jul. 21, 2022

(65) Prior Publication Data

US 2023/0414828 A1 Dec. 28, 2023

Related U.S. Application Data

(60) Provisional application No. 63/136,256, filed on Jan. 12, 2021.

(51) Int. Cl.
*A61L 27/18* (2006.01)
*A61L 27/50* (2006.01)

(52) U.S. Cl.
CPC ............... *A61L 27/18* (2013.01); *A61L 27/50* (2013.01); *A61L 2400/06* (2013.01); *A61L 2430/34* (2013.01)

(58) Field of Classification Search
CPC ...... A61L 27/18; A61L 27/50; A61L 2400/06; A61L 2430/34; A61L 27/58; A61L 27/60; A61K 8/062; A61K 8/42; A61K 8/731; A61K 8/891; A61K 2800/91; A61Q 19/08
See application file for complete search history.

(56) References Cited

U.S. PATENT DOCUMENTS

| | | | |
|---|---|---|---|
| 4,496,687 | A | 1/1985 | Okada et al. |
| 4,960,764 | A | 10/1990 | Figueroa, Jr. et al. |
| 5,300,286 | A | 4/1994 | Gee |
| 5,633,226 | A | 5/1997 | Owen et al. |
| 9,289,533 | B2 | 3/2016 | Schussler et al. |
| 9,993,578 | B1 * | 6/2018 | Loria |
| 2009/0169615 | A1 * | 7/2009 | Pinsky |
| 2010/0268189 | A1 | 10/2010 | Byrnes et al. |
| 2012/0189588 | A1 | 7/2012 | Nahas et al. |
| 2014/0079686 | A1 | 3/2014 | Barman et al. |
| 2014/0329913 | A1 | 11/2014 | Hanes et al. |
| 2015/0328288 | A1 | 11/2015 | Shoseyov et al. |
| 2016/0354516 | A1 | 12/2016 | Chuang |

OTHER PUBLICATIONS

International Search Report from corresponding PCT/US2022/012200 dated Apr. 1, 2022.
Chasan et al. (2007). The history of injectable silicone fluids for soft-tissue augmentation. Plastic and Reconstructive Surgery 120(7): pp. 2034-2040.
El-Hamouz et al. (2009). Dispersion of silicone oil in water surfactant solution: effect of impeller speed, oil viscosity and addition point on drop size distribution. Chemical Engineering and Processing: Process Intensification, 48.2, 633-642.
Fulton et al. (2012). The optimal filler: immediate and long-term results with emulsified silicone (1,000 centistokes) with cross-linked hyaluronic acid. Journal of drugs in dermatology: JDD 11.11: pp. 1336-1341.
Jones (2009). Semipermanent and permanent injectable fillers. Dermatologic clinics 27.4, 433-444.
Sasidaran et al. (2012). Low-grade liquid silicone injections as a penile enhancement procedure: Is bigger better?. Urology annals 4(3): pp. 181-186.
Schwartzberg et al. (2018). Safety of polysorbate 80 in the oncology setting. Adv Ther., 35(6): 754-767.
Vaziri et al. (2016). Tamponade in the surgical management of retinal detachment, Clinical Ophthalmology, 10, 471-476.
Wollina et al. (2015). Fillers for the improvement in acne scars. Clinical, cosmetic and investigational dermatology, 8, 493-499.
Yang et al. (2012). Tolerability and efficacy of newly developed penile injection of cross-linked dextran and polymethacrylate mixture on penile enhancement: 6 months follow up, International Journal of Impotence Research 25,3, 99-103.

* cited by examiner

*Primary Examiner* — Robert A Wax
*Assistant Examiner* — Kimberly Barber
(74) *Attorney, Agent, or Firm* — CAESAR RIVISE, PC

(57) ABSTRACT

A filler composition which is a pharmaceutically acceptable oil-in-water emulsion including 1-80 vol. % of a first silicone oil having a first viscosity; 15-98 vol. % of water, 1-3 wt. % of a transport medium; 0.05-10 vol. % of a surfactant; and optionally a second silicone oil having a second viscosity lower than the first. The second silicone oil is provided at 1-80 vol. % when the first viscosity is 30,000 cSt or less, or 0-80 vol. % when the first viscosity is greater than 30,000 cSt. At least one of the first silicone oil and the second silicone oil is dispersed in water as droplets having an average diameter of less than 30 microns. The transport medium is sufficiently biodegradable when implanted intradermally or subcutaneously in a human to provide a temporary scaffold for collagen growth between the droplets. A method of making the filler composition and a soft tissue augmentation method are also disclosed.

24 Claims, No Drawings

MULTIPLE VISCOSITY OIL-IN-WATER COMPOSITION USEFUL AS AN INJECTABLE FILLER AND A SCAFFOLD FOR COLLAGEN GROWTH

CROSS-REFERENCE TO RELATED APPLICATIONS

This application is a U.S. National Phase Application of PCT/US2022/012200 filed Jan. 12, 2022, which claims priority to U.S. Provisional Application No. 63/136,256 filed on Jan. 12, 2021, the contents of which are incorporated herein by reference in their entireties.

BACKGROUND OF THE INVENTION

1. Field of Invention

The invention generally relates to compositions comprising oil-in-water emulsions and to methods of making and using such compositions as a dermal filler. In particular, the invention relates to multiple viscosity oil-in-water emulsions that create an aggressive response producing collagen to surround the emulsified oil droplets while minimizing adverse reactions such as ulceration of the skin and fevers.

2. Description of Related Art

There has been a longstanding need, both medical and cosmetic, to develop materials and methods for soft tissue augmentation. The need or desire for this augmentation may vary, and may include, for example, the treatment of facial fine lines, wrinkles, and scars (such as acne scars), the reconstruction of soft tissue that has been damaged due to trauma (such as a hernia repair) or disease; the promotion of wound healing and tissue regeneration; the augmentation of breast tissue; and the enhancement of the male genitalia. Several materials and treatment techniques for soft tissue augmentation have been available at least since the mid-1900s. However, many of these materials and techniques have disadvantages.

Examples of treatment techniques include reconstructive surgery, implantation of prosthetics, and the injection of various materials. Surgical intervention may be used to repair or reconstruct tissue and may involve an autograft (where tissue is taken from one part of the patient's own body and transplanted into another) or an allograft (where the tissue is obtained from a non-identical donor). For example, allografts of human cadaver bone are often employed in dental procedures involving jawbone augmentation. Surgical intervention may also be used to reconstruct tissue and for the placement of implants and prosthetics. Examples of implants and prosthetics include those made from synthetic materials such as silicone, polyethylene, and polytetrafluoroethylene (an example of which is GORE-TEX) and those from naturally derived materials such as acellular dermal matrix (ADM), collagen, cadaver bone, and tissue parts from animal sources, such as porcine and bovine heart valves. Many of these treatment techniques are invasive and can lead to secondary medical issues.

In addition to surgical techniques, injection techniques employing needles or cannulas of various diameters have been used to inject patients with materials such as silicone oil, collagen, hyaluronic acid (an anionic, nonsulfated glycosaminoglycan distributed widely throughout connective, epithelial, and neural tissues), autologous fat (fat obtained from the same individual), calcium hydroxyapatite, poly-L-lactic acid, poly(methyl methacrylate), and botulinum toxin type A Botox. It is recognized that Botox injections are not technically used to augment tissue, but rather to provide their effects by blocking signals from the nerves to the muscles, which can help facial wrinkles to relax and soften. See, e.g., Jones, D., Semipermanent and Permanent Injectable Fillers, Dermatol Clin 27 (2009) 433-444.

However, these materials each have their own specific properties, longevity of treatment, and side effects. Some materials, such as collagen and autologous fat, tend to be temporary and are resorbed and require repeated treatments in the previous site at regular intervals. Other treatments, such as silicone oil, tend to be more permanent and do not break down as readily. Also, materials such as silicone oils appear to stimulate the production of the patient's own collagen, via a foreign body reaction, further adding to a greater and more natural tissue augmentation volume, filling, and permanence effect. See, e.g., U.S. Pat. No. 9,993,578 B1. Dermal fillers such as cross-linked dextran and poly (methyl methacrylate) (PMMA) have been reported. However, information seems to be lacking on the long-term effectiveness of this material for penile enhancement. See Yang, Y. et al., Tolerability and Efficacy of Newly Developed Penile Injection of Cross-linked Dextran and Polymethacrylate Mixture on Penile Enhancement, Int. J. Import. Res., 2013, 25(3), 99-103.

For effective soft tissue augmentation, it would be highly desirable to stimulate the production of high-quality collagen. Collagen is the main structural protein in the extracellular space in the various connective tissues in humans and animals. As the main component of connective tissue, it is the most abundant protein in mammals, making up from about 25% to 35% of the whole-body protein content. Depending upon the degree of mineralization, collagen tissue can be compliant or rigid. A single collagen molecule, also referred to as tropocollagen, is the component used to make up larger collagen aggregates, such as fibrils. These aggregates are arranged in different combinations and concentrations to provide varying tissue properties.

Depending on the area of the human body to be treated, it is generally desirable to stimulate the generation of new collagen that is preferentially produced and laid down as uniform, smooth sheets. Further, it is generally preferable that the formation of collagen occur in one to two weeks. The generation of such uniform and smooth collagen would be especially desirable in highly visible or sensitive areas of the body, such as the face, breasts, or male genitalia. In other cases, such as for surgical reconstruction and wound healing applications, structural integrity and tensile strength are important characteristics. A particular instance in which these structural and strength properties are important includes hernia repair, where the repair is subject to a great deal of constant mechanical stress. Therefore, it would also be highly desirable to provide compositions and methods for carefully controlling the quantity, structure, and quality of the collagen produced, depending on the application and outcome sought.

Certain types of silicone oils, when appropriately delivered, can stimulate the production of collagen. However, to generate appropriate collagen production, the physician or practitioner cannot simply place or inject a silicone oil into the target tissue of the patient.

The development of silicone oils and their use in medical and cosmetic procedures has a long and complicated history. See, e.g., Chasan, P., The History of Injectable Silicone Fluids for Soft-Tissue Augmentation, Plastic and Reconstructive Surgery, Volume 120, Number 7, pp. 2034-2040, December 2007. The first polydimethylsiloxanes were synthesized in the 1930s. Polydimethylsiloxanes (PDMS or silicone oil) can generally be described by the chemical formula, $CH_3[Si(CH_3)_2O]_nSi(CH_3)_3$, where n is the number of repeating monomer $[SiO(CH_3)_2]$ units. Polydimethylsiloxanes have many industrial applications, including their use as lubricants, antifoaming agents, and hydraulic fluids. In recent years, silicone oils found their way into personal care products such as hair and skin conditioners because of their substantive properties and smooth feel. See, e.g., U.S. Pat. Nos. 4,960,764 and 5,300,286.

The earliest use of silicones for tissue augmentation goes back to at least the time of the World War II when some women in Japan had silicone oil injections to augment their bustlines. The more controlled, medical use of injected silicones dates back to 1965 when Dow Corning obtained approval for investigation of its silicone oil, MDX 4-4011, in patients, for indications including the treatment of wrinkles and acne scars. Other studies were conducted on silicone oils for tissue augmentation. However, there is a paucity of rigorous scientific data, and various adverse reactions have been reported. Such adverse reactions include scarring, granuloma and nodule formation, inflammation, and migration or pooling of the silicone oil to and in the extremities, such as the legs. Granuloma formation is an inflammatory response, an extreme foreign body response, where the immune system attempts to wall off substances it perceives as foreign but is unable to eliminate them. From many of the studies it is difficult to determine whether the silicone oil itself, possible contaminants, or adulterants therein, the injection technique, or the quantity of silicone oil used was/were responsible for the adverse effects. Silicone oils, however, have, found successful use in ophthalmology as intraocular tamponades (i.e., as plugs or tampons) for treating retinal detachments. See, e.g., Vaziri, K. et al., Tamponade in the surgical management of retinal detachment, Clinical Ophthalmology 2016:10, pp. 471-476.

The literature reports a microdroplet technique, in which very small amounts (0.01 ml to 0.03 ml) of silicone oil are injected subcutis at intervals of 2 to 10 mm apart in the desired body site with a serial puncture technique, or up to about 1 ml is injected by a tunneling or fanning technique. However, the precise injection of small quantities of silicone oil can be tedious, and the end result highly dependent on the skill and judgment of the practitioner. There are reports of the use of this technique for male enhancement. See, e.g., Urol. Ann. 2012 September-December; 4(3): 181-186.doi: 10.4103/0974-7796.102672 PMCID: PMC3519113. Low-grade liquid silicone injections as a penile enhancement procedure: Is bigger better? Ramesh Sasidaran, Mohd Ali Mat Zain, and Normala Hj Basiron. Even in these instances, the quantities of injected silicone oil per injection site are still relatively large, and it can be difficult to achieve the uniformity desired for high quality collagen stimulation and production, thus resulting in a bumpy or nodular pattern, which is undesirable. In addition, it would be contraindicated to inject the penile skin with a microdroplet technique because of the subcutaneous space and the thin dermis.

Fulton et al. "The optimal filler: immediate and long-term results with emulsified silicone (1,000 centistokes) with cross-linked hyaluronic acid." Journal of drugs in dermatology: JDD 11.11 (2012): 1336-1341 discloses the use of silicone oil-in-water emulsions containing hyaluronic acid as injectable fillers for facial implantation.

Despite the foregoing developments, there is a need for the development of safe and effective compositions and methods for providing permanent soft tissue augmentation, and particularly for augmentation of more delicate and challenging sites such as the male genitalia. Preferably, these compositions and methods would stimulate the targeted tissue to produce sufficient quantities of high-quality collagen to permanently achieve the desired result.

All references cited herein are incorporated herein by reference in their entireties.

BRIEF SUMMARY OF THE INVENTION

Accordingly, a first aspect of the invention relates to a filler composition comprising: 1-80 vol. % of a first silicone oil having a first viscosity; 15-98 vol. % of water; 1-3 wt. % of a transport medium; 0.05-10 vol. % of a surfactant; and optionally a second silicone oil having a second viscosity lower than the first viscosity, wherein: the filler composition is a pharmaceutically acceptable oil-in-water emulsion; the second silicone oil is provided in an amount of 1-80 vol. % when the first viscosity is 30,000 cSt or less; the second silicone oil is provided in an amount of 0-80 vol. % when the first viscosity is greater than 30,000 cSt; at least one of the first silicone oil and the second silicone oil is dispersed in the water as droplets having an average diameter of less than 30 microns; and the transport medium is sufficiently biodegradable when implanted intradermally or subcutaneously in a human to provide a temporary scaffold for collagen growth between the droplets.

In certain embodiments, the composition comprises 3 vol. % of the second silicon oil and 27 vol. % of the first silicone oil, wherein the second viscosity is 1,000 cSt and the first viscosity is 12,500 cSt.

In certain embodiments, the composition comprises 5 vol. % of the second silicon oil and 25 vol. % of the first silicone oil, wherein the second viscosity is 12,500 cSt and the first viscosity is 100,000 cSt.

In certain embodiments, the composition comprises 30 vol. % of the first silicon oil and none of the second silicone oil, wherein the first viscosity is 100,000 cSt.

In certain embodiments, the first viscosity is from 12,500 cSt to 20,000,000 cSt and the second viscosity is from 65 cSt to 5000 cSt.

In certain embodiments, the first silicone oil and the second silicone oil are polydimethylsiloxane.

In certain embodiments, the transport medium is a water-soluble polymer.

In certain embodiments, the transport medium is at least one member selected from the group consisting of carboxymethylcellulose (CMC), hyaluronic acid, hydroxyethyl cellulose, methyl cellulose, hydroxypropylmethyl cellulose, polyvinylpyrrolidone, polyvinylalcohol, guar gum, hydroxypropyl guar gum, xanthan gum, croscarmellose sodium, and alginic acid.

In certain embodiments, the transport medium is CMC, which is optionally cross-linked.

In certain embodiments, the temporary scaffold dissolves in 7 to 35 days.

In certain embodiments, the surfactant is lidocaine.

In certain embodiments, the average diameter of the droplets is from 1 nanometer to 1 micron.

In certain embodiments, the first silicone oil and the second silicone oil are polydimethylsiloxane; the transport medium is an optionally cross-linked water-soluble polymer selected from the group consisting of carboxymethylcellulose (CMC), hyaluronic acid, hydroxyethyl cellulose, methyl cellulose, hydroxypropylmethyl cellulose, polyvinylpyrrolidone, polyvinylalcohol, guar gum, hydroxypropyl guar gum, xanthan gum, croscarmellose sodium, and alginic acid; the temporary scaffold dissolves in 7 to 35 days; the surfactant is lidocaine; and/or the average diameter of the droplets is from 1 nanometer to 1 micron.

A second aspect of the invention comprises a method for preparing the filler composition of the invention. The method comprises the steps of: (i) preparing an oil phase comprising the steps of: (a) providing an active ingredient that is substantially sterile and substantially free of pyrogen, wherein the active ingredient is the second silicone oil or the first silicone oil when there is no second silicone oil; (b) mixing the active ingredient with 1-5 volumes of sterile injectable water for 4 to 6 minutes at 1200 to 1500 rpm; (c) allowing the active ingredient and water mixture to separate into a lower water layer and an upper layer containing the active ingredient; (d) removing the lower water layer and collecting the upper layer; and (e) repeating steps (b) through (d) on the active ingredient at least once to obtain the oil phase; (ii) preparing a water phase solution comprising the sequential steps of: (a) dissolving with stirring a transport medium in a sterile solvent selected from the group consisting of injectable water, normal saline, Ringer's solution, and lactated Ringer's solution, to form a preliminary water phase solution; (b) sterilizing the preliminary water phase solution to form a sterilized water phase solution; and (c) optionally freezing and thawing the sterilized water phase solution; and (iii) preparing an oil-in-water emulsion by combining 35-45 parts by volume of the oil phase with 55-65 parts by volume of the water phase solution with agitation to form an emulsion of the active ingredient within the water.

In certain embodiments of the second aspect of the invention, the sterile solvent contains a cross-linking agent which forms cross-links in the transport medium.

In certain embodiments of the second aspect of the invention, the cross-linking agent is 1,4-butanediol diglycidyl ether in an amount from 0.01 to 10% by weight of the composition.

A third aspect of the invention comprises a soft tissue augmentation method comprising intradermally and/or subcutaneously injecting into a patient the inventive filler composition.

In certain embodiments of the third aspect of the invention, a volume of 20 to 60 ml of the filler composition is injected into a single injection site.

In certain embodiments of the third aspect of the invention: the filler composition stimulates collagen growth; the transport medium forms a temporary scaffold for collagen growth between active ingredient droplets; and a collagen matrix anchors the active ingredient droplets in place as the temporary scaffold dissolves within 7-35 days.

In certain embodiments of the third aspect of the invention, the filler composition is injected into a penis or a scrotum for penis or scrotum enhancement.

DETAILED DESCRIPTION OF THE INVENTION

The invention relates to compositions in the form of oil-in-water dispersions useful for stimulating collagen production in human patients and other mammals, which have applications for soft tissue augmentation for various medical and cosmetic procedures. The invention also relates to methods for preparing these compositions and to methods for stimulating collagen production in human patients and other mammals in need thereof. In contrast to the prior art, the compositions and methods of the present invention are particularly useful for stimulating the production of high quality collagen that is uniform, smooth, long-lasting, and has good structural integrity.

The compositions of the invention are useful for stimulating collagen production in a mammal in need thereof, and particularly in humans. The collagen stimulation can be for a variety of medical treatments or cosmetic effects, some non-limiting examples of which include: stimulating collagen production for penile or scrotal tissue enhancement; stimulating collagen production for face or body skin wrinkle reduction; stimulating collagen production to reduce or smooth cellulite; stimulating collagen production for scar repair; or stimulating collagen production for a hernia repair. Other nonlimiting applications include: stimulating collagen production for body or face enhancement, further exemplified by contouring the nose, ears, chin, cheeks, peri-orbital areas, forehead, drooping neck; recreation or enhancement of pectoral or abdominal musculature; buttock enhancement; filling or minimizing concave skin deformities, breast enhancement; hand rejuvenation; foot contouring—particularly thickening the bottom of the feet; intra articular joint treatments; tissue or injury repair; wound healing such as from burns or other trauma; promotion of healing and incorporation of prosthetics and implants; and inter or intra pleural treatment for conditions such as edema.

Definitions

The term "phagocytize" means to ingest by phagocytosis. Phagocytosis is a process by which certain living cells called phagocytes ingest or engulf other cells or particles. The phagocyte may be a free-living one-celled organism, such as an amoeba, or one of the body cells, such as a white blood cell.

The term "dispersion" means a system in which small particles or droplets are distributed or "dispersed" in a continuous phase, such as water. A dispersion can be classified in different ways, including particle size, whether or not precipitation occurs, and the presence of Brownian motion. A common example of a dispersion is a water-based ink. In the invention, the compositions include silicone oils dispersed in a water phase, which can be referred to as a silicone oil-in-water emulsion.

The term "emulsion" as used herein means a mixture of two or more liquids that are normally immiscible. Emulsions are part of a more general class of two-phase systems that are called colloids. An example of an emulsion is an oil-in-water ("o/w") emulsion in which the oil phase is dispersed in the continuous water phase. A common example of an emulsion is milk. In the invention, the compositions may also be in the form of oil-in-water emulsions wherein the oil phase is a silicone oil (i.e., a "silicone oil-in-water emulsion").

The term "surfactant" as used herein means a compound that lowers the surface tension between two liquids, between a gas and a liquid, or between a liquid and a solid, which may include other compounds that are not classified as surfactants but act similar to a surfactant. Surfactants may act as detergents, wetting agents, emulsifiers, foaming agents, or dispersants. In the invention, the compositions may use a surfactant to facilitate the creation of a silicone oil-in-water emulsion.

The term "viscosity" is used herein in its standard sense as a measure of the resistance of a fluid to gradual deformation by shear stress or tensile stress. The term is used in a more informal manner as the concept of the thickness of a fluid. The viscosity of a fluid can be reported as the dynamic, i.e., the absolute, viscosity or the kinematic viscosity. The dynamic viscosity of a fluid is typically reported in centistokes (cSt) and relates to the resistance of the fluid to shearing flows, where adjacent layers move parallel to each other with different speeds. The kinematic viscosity of a fluid is typically reported in centipoise (cP) and is the ratio of the dynamic viscosity to the density of the fluid. For example, a silicone fluid having a dynamic viscosity of 1000 cSt and a density of 0.90 g/ml would have a kinematic viscosity of 1111.11 cP (which is 1000 cSt divided by 0.90 g/ml). All viscosity values are provided as measured at 25° C. unless otherwise stated.

As used herein, use of the expression "pharmaceutically acceptable" to describe a material means that the material is suitable for use in contact with the tissues of humans and lower animals without undue toxicity, incompatibility, instability, irritation, allergic response and the like, commensurate with a reasonable benefit/risk ratio.

The term "biodegradable" describes a material capable of being dissolved when implanted in a human body.

The term "active ingredient" means a silicone oil or an analog known to those skilled in the art that causes a desired foreign body reaction. Although not desirable, an active ingredient may also cause an adverse reaction such as fevers, ulcerations, or the like. Most silicone oils will cause some adverse reactions to some degree when injected into the body, but for the purposes of the invention, the active ingredient is preferably be a silicone oil with a viscosity of less than 12,500 cSt.

The term "viscosity enhancer" refers to a silicone oil in a composition containing more than one type of silicon oil, wherein the viscosity enhancer is the silicone oil in the composition having the highest viscosity. The viscosity enhancer may be combined with the active ingredient to slow the migration and coalescence of oil phase droplets after injection to induce the foreign body reaction to occur.

The term "transport medium" means a substance that is able to transport the oil-in-water mixture to a selected injection site, reduce its migration and coalescence, and create a scaffold for collagen creation.

All percentages and ratios used herein, unless otherwise indicated, are by weight. It is also recognized that in certain instances it is useful and convenient to describe the compositions on a volume basis.

The invention may be embodied in other specific forms without departing from the spirit or essential characteristics thereof. The foregoing and following embodiments are to be considered in all respects illustrative rather than limiting on the invention described herein. In the various embodiments of the invention, such as for example, the compositions and methods of the invention, where the term comprises is used, it is also contemplated in other embodiments that the invention consists essentially of, or consists of, the embodiments. Further, it should be understood that the order of steps or order for performing certain actions is immaterial so long as the invention remains operable, unless specified otherwise. Moreover, two or more steps or actions can be conducted simultaneously in some instances.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

Preferred embodiments of the invention relate to multiple viscosity compositions in the form of oil-in-water emulsions optionally comprising an active ingredient, such as a silicone oil, having an average droplet diameter preferably less than 30 microns and a transport medium. The invention also relates to methods for preparing these compositions in the desired ratios and to methods for stimulating collagen production in human patients and other mammals in need thereof.

The compositions of the invention are particularly useful as soft tissue fillers which stimulate the production of high-quality collagen that is uniform, smooth, long lasting, and has good structural integrity.

The use of an oil-in-water emulsion aids in solving the common problem of lumps and irregularities forming after injection of silicone oil droplets. Silicone oil droplets with smaller diameters (preferably from 1 nanometer to 30 microns) can be delivered both intradermally and into the subcutaneous space of and under the skin more effectively with an emulsion, avoided the irregularities that commonly form when an emulsion is not used. The emulsion permits the oil droplets to be delivered close together with minimal to no migration or coalescence, allowing for a foreign body reaction FBR to take place and each droplet be encased in collagen. When droplets less than 30 microns are used without migration and the foreign body reaction takes place, collagen is formed in a smooth, continuous sheet. This result was unexpected in view of the previous understanding that if the silicone droplets were too small in size, i.e., under about 30 microns in diameter, the silicone oil would likely be ineffective, as the phagocytes would phagocytize the silicone oil, carrying it away before collagen production could be stimulated. See, e.g., U.S. Pat. No. 9,993,578 B1. However, further research indicates that smaller silicone droplets under 30 microns were not be removed from the body by the phagocytes. Clinical observations showed the foreign body response and collagen production occurred before the phagocytes could carry away the silicone oil.

Active Ingredient

The active ingredient is a silicone oil or an analog thereof that elicits a desired foreign body reaction.

Silicone oils are commercially produced with viscosities ranging from 0.65 to 2,500,000 cSt. One silicone oil discussed herein is PDMS which has a viscosity range of 0.65 to 100,000 cSt. In clinical situations, patients were injected with both lower viscosity and higher viscosity PDMS. The result observed was that a lower viscosity silicone oil (about 1,000 cSt) causes a more robust foreign body reaction including a more rapid response in the creation of collagen and the amount created at the location where the silicone was injected. This robust foreign body reaction has some adverse aspects, such as skin ulcerations and fevers. Further observations of patients with a higher viscosity silicone oil (about 12,500 cSt) showed a less robust foreign body reaction meaning the time to respond was increased and the amount of collagen produced was reduced. The higher viscosity silicone oil also produced a less robust foreign body reaction thereby minimizing the adverse reactions such as skin ulcerations and fevers.

To minimize adverse reactions with the use of silicone oil injections for soft tissue augmentation, efforts have been made to use more highly purified silicone oils and to minimize the injection amounts in any given tissue area. The purification efforts include the removal of pyrogens through techniques such as ion exchange chromatography, ultrafiltration, and distillation. Currently, silicone oil is used clinically for soft tissue augmentation of the lips and nasolabial folds (commonly known as “smile lines”) and to correct irregularities in the cheek and nose.

Another way to minimize the adverse reactions is combining a low viscosity silicone oil (sometimes referred to herein as a second silicone oil) with a higher viscosity silicone oil (sometimes referred to as a first silicone oil) at a desired ratio with the lower viscosity silicone oil preferably constituting a minor proportion of the combination. This combination also has the intended effect of promoting the rapid and increased production of collagen in human patients and other mammals while minimizing the adverse reactions. This composition is useful for soft tissue augmentation for various medical and cosmetic procedures including enlargement of the penis.

The silicone oils useful herein for stimulating collagen production are preferably selected from polydimethylsiloxanes, fluorinated polysiloxanes, dimethiconol, silicone polyethers, and mixtures thereof. Other silicone oils known to one skilled in the art may be useful in stimulation collagen production and useful in the invention. Polydimethylsiloxanes, also known as dimethicones, can generally be described by the chemical formula, $CH_3[Si(CH_3)_2O]nSi(CH_3)_3$, where n is the number of repeating monomer $[SiO(CH_3)_2]$ units. Examples of silicone oils particularly useful herein include polydimethylsiloxanes, which are generally classified with the CAS identification number 63148-62-9. Some commercially available polydimethylsiloxanes include ADATO SIL-OL 5000 Silicone Oil (Product Code ES-5000S, which is available from Bausch & Lomb, Rochester, NY). The material is described as a clear oily liquid with a viscosity of 5000 to 5900 centipoise (cP) at 25° C. and a specific gravity (density to water) of 0.913 at 25° C. A silicone oil with a viscosity of 5000 cP would have an approximate molecular weight of about 50,000 according to some sources.

Other polydimethylsiloxane materials include various Dow Corning silicone fluids such as Dow Corning Medical Fluids. However, some of these materials generally have a lower viscosity and are less desirable for use herein. Dow Corning fluids with preferable physical properties include Dow Corning 360 Medical Fluid 1000 cSt with a reported specific gravity (density compared to water) of 0.972 at 25° C.

Other polydimethylsiloxane materials include but are not limited to ALCON 1000 oil and SILIKON 1000 oil with preferable physical properties, including a viscosity of 1000 cSt and a reported specific gravity (density compared to water) of 0.97 at 25° C.

The active ingredient preferably constitutes 1-80% or 2-50% or 3-30% by volume of the filler composition.

Viscosity Enhancer

The viscosity enhancer is an oil having a viscosity higher than other silicone oil(s) in the filler composition. The viscosity enhancer is combined with the active ingredient to slow the migration and coalescence of oil phase droplets after injection to induce the foreign body reaction to occur.

The viscosity enhancer preferably has a viscosity from 12,500 cSt to 20,000,000 cSt.

The viscosity enhancer is preferably a higher molecular weight version of the oil used as the active ingredient Thus, the viscosity enhancer is preferably a silicone oil or analog thereof such as those described above with respect to the active ingredient, but having a viscosity of at least 12,500 cSt. The viscosity enhancer is most preferably polydimethylsiloxane, such as Dow Corning 360 Medical Fluid 12,500 cSt with a reported specific gravity (density compared to water) of 0.972 at 25° C.

The viscosity enhancer, like the active ingredient, may elicit a foreign body reaction after injection. However, any such foreign body reaction is less robust in the case of the viscosity enhancer and less likely to be accompanied by undesirable side effects, such as skin ulcerations and fever.

The viscosity enhancer, when provided in the filler composition, preferably comprises 1-80% or 10-50% or 20-30/a by volume of the filler composition.

The ratio of active ingredient to viscosity enhancer in the filler composition preferably ranges from 1:1000 to 100:1, or from 1:100 to 10:1, or from 1:10 to 1:1.

Transport Medium

Suitable transport mediums herein are generally polymeric transport mediums. Some of these transport mediums may be described as hydrophilic gelling agents or can generally be described as water-soluble or colloidally water-soluble polymers. Suitable transport mediums include but are not limited to hyaluronic acid, carboxymethylcellulose (i.e., CMC or cellulose gum) cellulose ethers (e.g., hydroxyethyl cellulose, methyl cellulose, hydroxypropylmethyl cellulose), polyvinylpyrrolidone, polyvinylalcohol, guar gum, hydroxypropyl guar gum, and xanthan gum. Additional non-limiting examples include croscarmellose sodium, which is an internally cross-linked sodium carboxymethylcellulose, and alginic acid, also called algin or alginate, which is an anionic polysaccharide that can be obtained from brown algae (seaweed).

The transport medium can be used either in its form as supplied (non-cross-linked) or can be cross-linked with a suitable crosslinking agent such as BDDE.

In exemplary embodiments using CMC cross-linked with BDDE, the CMC cross-linking permits the body to dissolve the CMC temporary scaffold in a slower fashion. This enables the immune system to systematically recognize each individual oil droplet and react via a foreign body reaction, encapsulating the oil droplet with collagen. After this reaction is repeated with each oil droplet, collagen is able to form in a smooth sheet as opposed to forming lumps or other irregularities In embodiments where cross-linked CMC is desired, the cross-linking agent (e.g., BDDE) is preferably used in an amount from 0.01% to 10% by weight or from 0.01% to 5% by weight or at about 0.1% by weight of the composition.

Other suitable transport mediums include, but are not limited to, acrylic acid/ethyl acrylate copolymers and the CARBOPOL carboxyvinyl polymers sold by Lubrizol Corp. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include CARBOPOL 934, CARBOPOL 940, CARBOPOL 950, CARBOPOL 980, CARBOPOL 951 and CARBOPOL 981. CARBOPOL 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available from Lubrizol Corp. as CARBOPOL 1382, CARBOPOL 1342 and PEMULEN TRI (CTFA Designation: Acrylates/10-30 Alkyl Acrylate Crosspolymer). A combination of the polyalkenyl polyether cross-linked acrylic acid polymer and the hydrophobically modified cross-linked acrylic acid polymer is also suitable. The transport mediums preferably provide excellent stability characteristics over both normal and elevated temperatures.

In certain embodiments, the transport medium comprises collagen modified to dissolve in vivo within a desired timeframe (e.g., 7-35 days). For example, the collagen can partially or completely hydrolyze to dissolve more quickly and can be crosslinked to decrease its dissolution rate. Preferably, the scaffold will dissipate within the body in a time frame consistent with the time required for the foreign body reaction to lay down a uniform collagen layer.

The transport medium preferably comprises 0.5-5 wt. % or 1-3 wt. % of the filler composition.

Surfactant

The surfactant facilitates the mixing of the oils and the water to create a stable injectable emulsion. The surfactant preferably comprises at least one member selected from the group consisting of anionic, amphoteric, nonionic and cationic compounds. Lidocaine hydrochloride (HCL) and analogs thereof are preferably included to provide both surfactant action and pain relief at the injection sites. The surfactant preferably constitutes from 0.001% to 10% of the water phase.

Polysorbate is another suitable surfactant. Polysorbates are hydrophilic nonionic surfactants that are oily liquids derived from ethoxylated sorbitan (a derivative of sorbitol) esterified with fatty acids. Common brand names for polysorbates include Scattics, Alkest, Canarcel. The names of polysorbates are commonly followed by a number which relates to the number of repeating units in the molecules. Polysorbates have been used in foods and in injectable medications such as oncology drugs. See "Safety of Polysorbate80 in the Oncology Setting," Lee S. Schwartzberg and Rudolph M. Navari, Adv Ther. 2018; 35(6): 754-767. Published online 2018 May 23.

The surfactant should preferably decrease the size of the droplets to an average diameter less than 30 microns. In certain embodiments, lidocaine is used as the surfactant to combine the water and the silicone oils with the added benefit of providing the human patients and other mammals with an analgesic effect.

The surfactant preferably constitutes from 0.05 vol. % to 10 vol. % of the filler composition.

Water

The filler composition preferably comprises water in an amount by weight from 15% to 98%, or from 30% to 95%, or from 50% to 80%. The water is preferably pharmaceutical grade and preferably USP water for injection.

Additional Components

The compositions of the invention may include additional components, including, but not limited to salts, sugars, buffers, alcohols, preservatives, anti-oxidants, and UV-absorbers. The exact amounts and materials chosen may be determined by one of skill in the formulation art to achieve a formulation with the desired characteristics.

Additional components can include solvents such as ethanol, glycerol, and propylene glycol; stabilizers such as ethylene diamine tetraacetic acid (EDTA) and citric acid; antimicrobial preservatives such as benzyl alcohol; methyl paraben, and propyl paraben; antioxidants such as butylated hydroxyanisole (BHA) and butylated hydroxytoluene (BHT); buffering agents such as citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers such as sodium chloride, mannitol, and dextrose. The exact levels of the additional components would generally be less than about 1% by weight of the total composition but can vary depending on the desired final composition and the target physical and physiological properties.

In other embodiments of the invention, other additional components can include, for example those used to make a normal saline solution, which is isotonic to have an osmolality of a human cell. A normal saline solution contains about 154 mmol/L of sodium ion and about 154 mmol/L of chloride ion. The compositions of the invention can be formulated to have a final composition for the foregoing components to essentially be equivalent to a normal saline solution. Normal saline has a pH of about 5.

In yet other embodiments of the invention, other additional components, can include, for example, those used to make Ringer's solution, particularly lactated Ringer's solution, which is isotonic with human blood, is compatible with human tissue, and is suitable for injection. Lactated Ringer's solution contains about 130 mmol/L of sodium ion, about 109 mmol/L of chloride ion, about 28 mmol/L of lactate ion, about 4 mmol/L of potassium ion, and about 1.5 mmol/L of calcium ion. The compositions of the invention can be formulated to have a final composition for the foregoing components to essentially be equivalent to lactated Ringer's solution. Lactated Ringer's solution has a pH of about 6.5.

The compositions of the invention will generally have physical parameters that have been optimized for physical characteristics of the compositions, and the safety and efficacy of the composition.

The filler composition of the invention preferably has a suitable viscosity to be readily injectable using a suitable gauge needle or cannula, e.g., a 14-gauge, 18-gauge and/or 25-gauge needle or cannula. The viscosity is preferably at least 100 cSt.

Filler compositions of the invention should have a pH and tonicity that is physiologically compatible with the tissue of the subject into which the material is to be injected, to thereby minimize discomfort and the potential for tissue damage. Suitable pH may range from approximately 4.5 to about 7. The tonicity of the compositions should generally be isotonic with human blood or human cell. One suitable target for tonicity and pH is based on the composition of a normal saline solution, as described above. Another suitable target for tonicity and pH is based on the composition of a lactated Ringer's solution, as described above.

It is particularly preferred that the compositions have an oil droplet size (i.e., diameter) within appropriate ranges to ensure the stimulation of sufficiently high-quality collagen with desired properties. The compositions of the invention are prepared to have dispersed oil droplets of a desired size range. As discussed above, droplets that are too large are undesirable, and an even distribution of droplet size is preferred. The droplet size of the dispersed oil droplets can be determined by microscopy and other techniques available to one of skill in the art. The droplet size can be reported as an average or mean size and can be reported with a distribution of size range.

Droplets having diameters from 30 microns to 1000 microns will provide very good natural feeling clinical results with a good quantity of collagen production. Droplets having diameters of less than 30 microns provide very good natural feeling clinical results plus a greater amount of collagen production due to the volume of collagen surrounding the smaller droplets which would be greater than volume of collagen surrounding the same volume of those smaller droplets if all were coalesced into one droplet. Thus, greater girth gains will be realized per treatment with the droplet diameters less than 30 microns. Accordingly, preferred compositions of the invention have an average oil droplet diameter of 1000 microns or less, or from 1 to 1000 microns. More preferred compositions of the invention have an average oil droplet diameter less than 30 microns, preferably from 1 nanometer to 30 microns, or 1-29 microns.

The compositions of the invention preferably have suitable stability, including storage stability, stability during use and injection, and stability once injected. In some embodiments, it is desirable to freeze the compositions for storage. Preferably, the compositions can be stored for up to about 45 days after which further FDA physical and chemical stability testing could be required. When the product is frozen, it is then thawed prior to use. The FDA generally requires that compound products be used within 72 hours of preparation or thawing.

Compositions of the invention are preferably biodegradable when implanted within a human or other lower animal. In particular, the transport medium component of the composition may be selected to degrade (e.g., dissolve) when implanted in a host, so as to allow host tissues, including nascent collagen, progressively greater access to the oil droplets over time. In this way, the composition provides a temporary scaffold for collagen growth between oil droplets.

The time it takes for the scaffold to dissolve can be adjusted through the selection of the transport medium. The scaffold may dissolve in an amount of time ranging from 7 to 365 days. A shorter time frame is most preferred for penile shaft-glans-scrotal enlargement, considering that sexual activity involving physical stimulation of the enlarged regions is to be avoided until the scaffold has dissolved.

The rate of biodegradation of the transport medium may be adjusted, e.g., through the selection of the transport medium, adjusting the chain length of the transport medium and adjusting the degree of crosslinking in the transport medium. Long-lasting highly crosslinked dermal fillers, such as JUVEDERM and RESTYLANE, will result in scaffolds that dissolve too slowly for penile shaft-glans-scrotal enlargement. On the other hand, if the transport medium dissolves too rapidly, the oil droplets will increase in migration capability, permitting them to coalesce form major lumps. In these instances, a lower amount of collagen will be formed. One exemplary embodiment may form many small oil droplets surrounded by collagen rather than one large oil droplet surrounded by collagen, as the amount of collagen formed around the small oil droplets will be much more in total.

Preparation Method

The compositions of the invention are prepared by the following general procedure, although other embodiments are contemplated. In certain embodiments, the oil-in water dispersions are prepared by separately preparing the oil and water phases and combining these phases with appropriate mixing.

In the preferred embodiment wherein the active ingredient is a silicone oil, the process includes the general steps of: 1) preparing each silicone oil phase fraction including the steps of: (a) sterilizing and depyrogenizing each oil fraction until essentially sterile and pyrogen-free; (b) washing each oil fraction by mixing the resultant sterile and pyrogen-free fraction with a volume of sterile injectable water ranging from about an equal volume to about four to five volumes, for approximately 5 minutes while mixing at a range of 1200 to 1500 rpm; (c) allowing each oil fraction and water mixture to separate into two layers; (d) removing the lower water layer and collecting the upper silicone layer (so as to remove lower molecular weight molecules produced from the manufacturing of the viscosity enhancer and thus significantly reduce the potential chemical toxicity (pyrogens) and/or allergic reactions from the viscosity enhancer); (e) optionally repeating the foregoing steps one or more additional times to sufficiently reduce the pyrogens to an acceptable level to minimize adverse reactions; (f) combining each of the oil phase fractions to obtain the silicone oil phase; 2) preparing a water phase comprising the steps of: (a) dissolving a transport medium in sterile injectable water or a sterile solution selected from normal saline, Ringer's solution, or lactated Ringers solution, solution with stirring to form a thickened water phase solution, (b) sterilizing the thickened water phase solution, (c) optionally freezing and thawing the sterilized thickened water phase solution, (d) adding any other desired components such as surfactant, potentially comprising lidocaine; and 3) preparing a silicone oil in water dispersion comprising the step of adding approximately 40 parts by volume of the silicone oil phase to approximately 60 parts by volume of the thickened water phase with agitation to form a dispersion of the silicone oil within the water.

The above procedure can be readily modified to incorporate a crosslinking agent for the transport medium, via the alternative for steps (a) through (c) of 2) above, as follows with steps (a) through (d): 2) preparing a water phase comprising the steps of: (a) dissolving a crosslinking agent in sterile injectable water or a sterile solution selected from normal saline, Ringer's solution, or lactated Ringers solution with stirring to form a solution of the crosslinking agent; (b) dissolving a transport medium in the solution of the crosslinking agent to form a thickened water phase solution; (c) sterilizing the thickened water phase solution; and (d) optionally freezing and thawing the sterilized thickened water phase solution.

The above procedures can also be readily modified to switch the positions of the viscosity enhancer and the active ingredient, where the active ingredient replaces the viscosity enhancer in steps (a) through (f) of (i) above and viscosity enhancer replaces the active ingredient of step (f).

In certain exemplary embodiments, the thickened water phase solution is sterilized at 170° C. In further embodiments, the sterilization may occur in an oven.

In certain exemplary embodiments, mixing may occur in an autoclave.

Soft Tissue Augmentation Method

The soft tissue augmentation method of the invention comprises intradermally and/or subcutaneously injecting into a patient the filler composition of the invention.

The volume of filler composition injected into a single injection site is preferably from 1 to 75 ml, or from 20 to 60 ml.

The filler composition stimulates collagen growth, with the transport medium preferably forming a temporary scaffold for collagen growth between oil droplets such that a collagen matrix forms to anchor the oil droplets in place as the temporary scaffold dissolves within 7-35 days.

The method can be used for penis enhancement, scrotum enhancement, filling wrinkles or depressions in the face or body, repairing scars, repairing hernias and breast augmentation.

While the invention has been described in detail and with reference to specific examples thereof, it will be apparent to one skilled in the art that various changes and modifications can be made therein without departing from the spirit and scope thereof.

What is claimed is:

1. A filler composition comprising:

1-80 vol. % of a first silicone oil having a first viscosity of 12,500 to 20,000,000 cSt;

15-98 vol. % of water;

1-3 wt. % of a transport medium;

0.05-10 vol. % of a surfactant; and optionally a second silicone oil having a second viscosity lower than the first viscosity, wherein:

the filler composition is free of collagen;

the filler composition is a pharmaceutically acceptable oil-in-water emulsion;

at least one of the first silicone oil and the second silicone oil is dispersed in the water as droplets having an average diameter of less than 30 microns; and the transport medium is sufficiently biodegradable when implanted intradermally or subcutaneously in a human to provide a temporary scaffold for collagen growth between the droplets.

2. The filler composition of claim 1, which comprises 3 vol. % of the second silicone oil and 27 vol. % of the first silicone oil, wherein the second viscosity is 1,000 cSt and the first viscosity is 12,500 cSt.

3. The filler composition of claim 1, which comprises 5 vol. % of the second silicone oil and 25 vol. % of the first silicone oil, wherein the second viscosity is 12,500 cSt and the first viscosity is 100,000 cSt.

4. The filler composition of claim 1, which comprises 30 vol. % of the first silicone oil and none of the second silicone oil, wherein the first viscosity is 100,000 cSt.

5. The filler composition of claim 1, wherein the second viscosity is from 65 cSt to 5000 cSt.

6. The filler composition of claim 1, wherein the first silicone oil and the second silicone oil are polydimethylsiloxane.

7. The filler composition of claim 1, wherein the transport medium is a water-soluble polymer.

8. The filler composition of claim 1, wherein the transport medium is at least one member selected from the group consisting of carboxymethylcellulose (CMC), hyaluronic acid, hydroxyethyl cellulose, methyl cellulose, hydroxypropylmethyl cellulose, polyvinylpyrrolidone, polyvinylalcohol, guar gum, hydroxypropyl guar gum, xanthan gum, croscarmellose sodium, and alginic acid.

9. The filler composition of claim 8, wherein the transport medium is CMC.

10. The filler composition of claim 9, wherein the CMC is cross-linked.

11. The filler composition of claim 1, wherein the temporary scaffold dissolves in 7 to 35 days.

12. The filler composition of claim 1, wherein the surfactant is lidocaine.

13. The filler composition of claim 1, wherein the average diameter of the droplets is from 1 nanometer to 1 micron.

14. The filler composition of claim 1, wherein:

the first silicone oil and the second silicone oil are polydimethylsiloxane;

the transport medium is an optionally cross-linked water-soluble polymer selected from the group consisting of carboxymethylcellulose (CMC), hyaluronic acid, hydroxyethyl cellulose, methyl cellulose, hydroxypropylmethyl cellulose, polyvinylpyrrolidone, polyvinylalcohol, guar gum, hydroxypropyl guar gum, xanthan gum, croscarmellose sodium, and alginic acid;

the temporary scaffold dissolves in 7 to 35 days;

the surfactant is lidocaine; and/or the average diameter of the droplets is from 1 nanometer to 1 micron.

15. A method for preparing the filler composition according to claim 1, comprising the steps of:

(i) preparing an oil phase comprising the steps of:

(a) providing at least one silicone oil that is substantially sterile and substantially free of pyrogen, wherein the at least one silicone oil comprises the first silicone oil and optionally the second silicone oil;

(b) mixing the at least one silicone oil with 1-5 volumes of sterile injectable water for 4 to 6 minutes at 1200 to 1500 rpm;

(c) allowing the at least one silicone oil and water mixture to separate into a lower water layer and an upper layer containing the at least one silicone oil;

(d) removing the lower water layer and collecting the upper layer; and (e) repeating steps (b) through (d) on the at least one silicone oil at least once to obtain the oil phase;

(ii) preparing a water phase solution comprising the sequential steps of:

(a) dissolving with stirring a transport medium in a sterile solvent selected from the group consisting of injectable water, normal saline, Ringer's solution, and lactated Ringer's solution, to form a preliminary water phase solution;

(b) sterilizing the preliminary water phase solution to form a sterilized water phase solution; and (c) optionally freezing and thawing the sterilized water phase solution; and (iii) preparing an oil-in-water emulsion by combining 35-45 parts by volume of the oil phase with 55-65 parts by volume of the water phase solution with agitation to form an emulsion of the at least one silicone oil within the water.

16. The method of claim 15, wherein the sterile solvent contains a cross-linking agent which forms cross-links in the transport medium.

17. The method of claim 16, wherein the cross-linking agent is 1,4-butanediol diglycidyl ether in an amount from 0.01 to 10% by weight of the composition.

18. A soft tissue augmentation method comprising intradermally and/or subcutaneously injecting into a patient the filler composition of claim 1.

19. The soft tissue augmentation method of claim 18, wherein a volume of 20 to 60 ml of the filler composition is injected into a single injection site.

20. The soft tissue augmentation method of claim 18, wherein:

the filler composition stimulates collagen growth;

the transport medium forms a temporary scaffold for collagen growth between the droplets; and a collagen matrix anchors the droplets in place as the temporary scaffold dissolves within 7-35 days.

21. The soft tissue augmentation method of claim 18, wherein the filler composition is injected into a penis or a scrotum for penis or scrotum enhancement.

22. A filler composition comprising:

1-80 vol. % of at least one silicone oil having a viscosity between 5,000 cSt and 30,000 cSt;

15-98 vol. % of water;

1-3 wt. % of a transport medium;

0.05-10 vol. % of a surfactant, wherein:

the filler composition is a pharmaceutically acceptable oil-in-water emulsion;

the at least one silicone oil is dispersed in the water as droplets having an average diameter of less than 30 microns; and the transport medium is sufficiently biodegradable when implanted intradermally or subcutaneously in a human to provide a temporary scaffold for collagen growth between the droplets.

23. The filler composition of claim 22, wherein the viscosity of the at least one silicone oil is between 5,000 cSt and 12,500 cSt.

24. The filler composition of claim 23, wherein the transport medium is at least one member selected from the group consisting of carboxymethylcellulose (CMC), hyaluronic acid, hydroxyethyl cellulose, methyl cellulose, hydroxypropylmethyl cellulose, polyvinylpyrrolidone, polyvinylalcohol, guar gum, hydroxypropyl guar gum, xanthan gum, croscarmellose sodium, and alginic acid, and the surfactant is lidocaine.

* * * * *